(12) United States Patent
Ostroff et al.

(10) Patent No.: US 8,014,851 B2
(45) Date of Patent: Sep. 6, 2011

(54) SIGNAL ANALYSIS IN IMPLANTABLE CARDIAC TREATMENT DEVICES

(75) Inventors: Alan H. Ostroff, San Clemente, CA (US); James W. Phillips, Fountain Valley, CA (US); Venugopal Allavatam, Oceanside, CA (US)

(73) Assignee: Cameron Health, Inc., San Clemente, CA (US)

( * ) Notice: Subject to any disclaimer, the term of this patent is extended or adjusted under 35 U.S.C. 154(b) by 1318 days.

(21) Appl. No.: 11/527,184

(22) Filed: Sep. 26, 2006

(65) Prior Publication Data

US 2008/0077030 A1 Mar. 27, 2008

(51) Int. Cl.
*A61B 5/0464* (2006.01)

(52) U.S. Cl. .......................... 600/515; 607/9

(58) Field of Classification Search .......... 600/515–518, 600/521
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Weilders et al. |
| 4,567,900 A | 2/1986 | Moore |
| 4,589,420 A | 5/1986 | Adams et al. |

(Continued)

FOREIGN PATENT DOCUMENTS

DE 298 01 807 U1 7/1998

(Continued)

OTHER PUBLICATIONS

Bardy, Gust H. et al., "Multicenter Experience with a Pectoral Unipolar Implantable Cardioverter-Defibrillator," *JACC*, Aug. 1996, vol. 28, No. 2, pp. 400-410.

(Continued)

*Primary Examiner* — Carl H Layno
*Assistant Examiner* — Jessica Sarcione
(74) *Attorney, Agent, or Firm* — Pramudji Law Group PLLC; Ari Pramudji; Mark Schroeder

(57) ABSTRACT

Methods and devices for cardiac signal analysis in implantable cardiac therapy systems. Several signal processing and/or conditioning methods are shown including R-wave detection embodiments including the use of thresholds related to previous peak amplitudes. Also, some embodiments include sample thresholding to remove extraneous data from sampled signals. Some embodiments include weighting certain samples more heavily than other samples within a sampled cardiac signal for analysis.

6 Claims, 9 Drawing Sheets

U.S. PATENT DOCUMENTS

| | | |
|---|---|---|
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,800,883 A | 1/1989 | Winstrom |
| 4,830,005 A | 5/1989 | Woskow |
| 4,944,300 A | 7/1990 | Saksena |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,300,106 A | 4/1994 | Dahl et al. |
| 5,313,953 A | 5/1994 | Yomtov et al. |
| 5,331,966 A | 7/1994 | Bennett et al. |
| 5,339,820 A | 8/1994 | Henry et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,439,485 A | 8/1995 | Mar et al. |
| 5,447,521 A | 9/1995 | Anderson et al. |
| 5,476,503 A | 12/1995 | Yang |
| 5,486,199 A | 1/1996 | Kim et al. |
| 5,509,923 A | 4/1996 | Middleman et al. |
| 5,509,928 A | 4/1996 | Acken |
| 5,522,852 A | 6/1996 | White et al. |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,755,738 A | 5/1998 | Kim et al. |
| 5,766,226 A | 6/1998 | Pedersen |
| 5,776,169 A | 7/1998 | Schroeppel |
| 5,814,090 A | 9/1998 | Latterell et al. |
| 5,827,197 A | 10/1998 | Bocek et al. |
| 5,827,326 A | 10/1998 | Kroll et al. |
| 5,836,976 A | 11/1998 | Min et al. |
| 5,843,132 A | 12/1998 | Ilvento |
| 5,891,171 A | 4/1999 | Wickham |
| 5,895,414 A | 4/1999 | Sanchez-Zambrano |
| 5,904,705 A | 5/1999 | Kroll et al. |
| 5,913,880 A | 6/1999 | Vonk |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,991,657 A | 11/1999 | Kim |
| 5,999,853 A | 12/1999 | Stoop et al. |
| 6,014,586 A | 1/2000 | Weinberg et al. |
| 6,016,446 A | 1/2000 | Belalcazar |
| 6,026,325 A | 2/2000 | Weinberg et al. |
| 6,029,086 A | 2/2000 | Kim et al. |
| 6,038,474 A | 3/2000 | Zhu et al. |
| 6,041,251 A | 3/2000 | Kim et al. |
| 6,047,210 A | 4/2000 | Kim et al. |
| 6,052,617 A | 4/2000 | Kim |
| 6,058,327 A | 5/2000 | Borgerding et al. |
| 6,058,328 A | 5/2000 | Levine et al. |
| 6,093,173 A | 7/2000 | Balceta et al. |
| 6,095,987 A | 8/2000 | Shmulewitz et al. |
| H1905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |
| 6,169,918 B1 | 1/2001 | Haefner et al. |
| 6,185,450 B1 | 2/2001 | Seguine et al. |
| 6,249,701 B1 | 6/2001 | Rajasekhar et al. |
| 6,266,554 B1 | 7/2001 | Hsu et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,282,446 B1 | 8/2001 | Eberle et al. |
| 6,334,071 B1 | 12/2001 | Lu |
| 6,345,198 B1 | 2/2002 | Mouchawar et al. |
| 6,393,316 B1 | 5/2002 | Gillberg et al. |
| 6,411,844 B1 | 6/2002 | Kroll et al. |
| 6,418,343 B1 | 7/2002 | Zhang et al. |
| 6,434,426 B1 | 8/2002 | Munneke et al. |
| 6,625,490 B1 | 9/2003 | McClure et al. |
| 6,647,292 B1 | 11/2003 | Bardy et al. |
| 6,650,931 B1 | 11/2003 | McClure et al. |
| 6,708,058 B2 | 3/2004 | Kim et al. |
| 6,721,597 B1 | 4/2004 | Bardy et al. |
| 6,745,076 B2 | 6/2004 | Wohlgemuth et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,856,835 B2 | 2/2005 | Bardy et al. |
| 6,862,476 B2 | 3/2005 | Mouchawar et al. |
| 6,865,417 B2 | 3/2005 | Rissmann et al. |
| 6,866,044 B2 | 3/2005 | Bardy et al. |
| 6,889,079 B2 | 5/2005 | Bocek et al. |
| 6,892,092 B2 | 5/2005 | Palreddy et al. |
| 6,927,721 B2 | 8/2005 | Ostroff et al. |
| 6,937,907 B2 | 8/2005 | Bardy et al. |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,980,856 B2 | 12/2005 | Sullivan et al. |
| 6,988,003 B2 | 1/2006 | Bardy et al. |
| 6,996,434 B2 | 2/2006 | Marcovecchio et al. |
| 7,020,523 B1 | 3/2006 | Lu et al. |
| 7,027,858 B2 | 4/2006 | Cao et al. |
| 7,031,764 B2 | 4/2006 | Schwartz et al. |
| 7,039,459 B2 | 5/2006 | Bardy et al. |
| 7,039,463 B2 | 5/2006 | Marcovecchio |
| 7,043,299 B2 | 5/2006 | Erlinger et al. |
| 7,062,329 B2 | 6/2006 | Ostroff |
| 7,065,407 B2 | 6/2006 | Bardy et al. |
| 7,065,410 B2 | 6/2006 | Bardy et al. |
| 7,069,080 B2 | 6/2006 | Bardy et al. |
| 7,076,294 B2 | 7/2006 | Bardy et al. |
| 7,076,296 B2 | 7/2006 | Rissmann et al. |
| 7,085,599 B2 | 8/2006 | Kim et al. |
| 7,090,682 B2 | 8/2006 | Sanders et al. |

| | | |
|---|---|---|
| 7,092,754 B2 | 8/2006 | Bardy et al. |
| 7,162,301 B2 | 1/2007 | Kim et al. |
| 7,184,815 B2 | 2/2007 | Kim et al. |
| 7,184,818 B2 | 2/2007 | Kim et al. |
| 7,191,004 B2 | 3/2007 | Kim et al. |
| 2002/0091333 A1* | 7/2002 | Hsu et al. ............ 600/518 |
| 2004/0254611 A1 | 12/2004 | Palreddy et al. |
| 2004/0254613 A1 | 12/2004 | Ostroff et al. |
| 2005/0049644 A1 | 3/2005 | Warren et al. |
| 2005/0131476 A1 | 6/2005 | Kim et al. |
| 2005/0131478 A1 | 6/2005 | Kim et al. |
| 2005/0149125 A1 | 7/2005 | Kim et al. |
| 2006/0036288 A1 | 2/2006 | Bocek et al. |
| 2006/0074331 A1 | 4/2006 | Kim et al. |
| 2006/0085038 A1 | 4/2006 | Linder et al. |
| 2006/0178704 A1 | 8/2006 | Elahi et al. |
| 2006/0217621 A1 | 9/2006 | Kim et al. |
| 2006/0259089 A1 | 11/2006 | Kim et al. |
| 2007/0038253 A1 | 2/2007 | Kim et al. |

FOREIGN PATENT DOCUMENTS

| | | |
|---|---|---|
| EP | 0 095 727 A1 | 12/1983 |
| EP | 0 316 616 A2 | 5/1989 |
| EP | 0 347 353 A1 | 12/1989 |
| EP | 0 517 494 B1 | 12/1992 |
| EP | 0 518 599 A2 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/24275 A2 | 3/2002 |
| WO | WO 02/068046 A1 | 9/2002 |
| WO | WO 03/018121 A2 | 3/2003 |

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Higgins, Steven L. et al., "The First Year Experience with the Dual Chamber ICD," *PACE*, Jan. 2000, vol. 23, pp. 18-25.

Mirowski, M. et al., "Automatic Detection and Defibrillation of Lethal Arrhythmias—A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999)vol. 88, No. 8, pp. 559-565.

Throne, Robert D., "A Comparison of Four New Time-Domain Techniques for Discriminating Monomorphic Ventricular Tachycardia from Sinus Rhythm Using Ventricular Waveform Morphology," *IEEE Transactions on Biomedical Engineering*, vol. 38, No. 6, Jun. 1991, pp. 561-570.

Tietze U. et al., "Halbleiter-Schaltungstechnik," ©Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.

Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.

* cited by examiner $$T_R \times W = T_W$$

$$\begin{bmatrix} 0.4 & 1.2 & 1.5 & 0.3 \end{bmatrix} \times \begin{bmatrix} 1 & 0 & 0 & 0 \\ 0 & 1.5 & 0 & 0 \\ 0 & 0 & 1.5 & 0 \\ 0 & 0 & 0 & 1 \end{bmatrix} = \begin{bmatrix} 0.4 & 1.8 & 2.25 & 0.3 \end{bmatrix}$$

$$S_R \times W = S_W$$

$$\begin{bmatrix} 0.5 & 1.1 & 1.4 & 0.4 \end{bmatrix} \times \begin{bmatrix} 1 & 0 & 0 & 0 \\ 0 & 1.5 & 0 & 0 \\ 0 & 0 & 1.5 & 0 \\ 0 & 0 & 0 & 1 \end{bmatrix} = \begin{bmatrix} 0.5 & 1.65 & 2.1 & 0.4 \end{bmatrix}$$

FIG. 8

SIGNAL ANALYSIS IN IMPLANTABLE CARDIAC TREATMENT DEVICES

FIELD

The present invention is related to the field of implantable medical devices. More particularly, the present invention relates to methods of analyzing cardiac signals.

BACKGROUND

Pacemakers and implantable cardioverter/defibrillators (ICDs) have become useful treatment devices for those with cardiac dysfunction. These devices provide electrical stimulus that helps a patient's heart function properly. One aspect of such devices is the desire to accurately identify whether and when a patient is experiencing a malignant cardiac condition. However, the heart may experience not only normal sinus rhythms but also various forms of arrhythmias, such as atrial fibrillation, atrial tachycardias, ventricular fibrillation, and ventricular tachycardias. Not all of these arrhythmias are malignant. Because the application of cardioversion or defibrillation stimulus can be discomforting to a patient, unnecessary application of stimulus should be avoided. Further, erroneous application of stimulus can cause a patient's heart to enter a malignant cardiac condition such as fibrillation. Methods and devices that provide additional approaches to discriminating between malignant and non-malignant cardiac conditions are therefore desired.

SUMMARY

The present invention, in an illustrative embodiment, includes a method of cardiac signal analysis, the method comprising capturing a cardiac signal by the use of first and second electrodes disposed within a patient, detecting a cardiac event, conditioning a portion of the cardiac signal associated with the cardiac event, and analyzing the portion of the cardiac signal to determine whether the patient is likely experiencing a malignant cardiac condition. The step of conditioning a portion of the cardiac signal associated with the cardiac event may include sampling the cardiac signal to generate a number of samples and comparing a selected sample to a sample threshold and, if the sample magnitude does not exceed the sample threshold, replacing the sample with a different value.

In some embodiments, the samples are at least temporarily stored in a form having a least amplitude and a greatest amplitude, wherein, if the sample magnitude does not exceed the sample threshold, the method includes replacing the selected sample with a value corresponding to the least amplitude. In another embodiment, the samples are at least temporarily stored in a signed format, wherein, if the sample magnitude does not exceed the sample threshold, the method includes replacing the selected sample with a value corresponding to a zero in the signed format. If the sample magnitude does not exceed the sample threshold, the method may include replacing the selected sample with a value corresponding to the sample threshold.

In some embodiments, the step of analyzing the portion of the cardiac signal includes comparing the portion of the cardiac signal to a stored template, wherein the stored template includes a number of template samples and, if one or more of the template samples do not exceed the threshold, those template samples are marked, and the selected sample of the portion of the cardiac signal is selected such that it corresponds to a marked sample of the template when the portion of the cardiac signal is compared to the stored template. The method may further include weighting the sample vector to give some signal samples greater analytical weight than others. In some embodiments, the step of analyzing the portion of the cardiac signal may include a step of comparing the portion of the cardiac signal to a stored template and the comparing step includes weighting certain samples of the portion of the cardiac signal more than other samples.

The present invention, in another illustrative embodiment, includes a method of cardiac signal analysis, the method comprising capturing a cardiac signal by the use of first and second electrodes disposed within a patient, detecting a cardiac event, sampling the cardiac signal, treating the sampled signal as a sample vector, and multiplying the sample vector by a weighting vector to yield a weighted sample vector, and analyzing the weighted sample vector to determine whether the patient is likely experiencing a malignant cardiac condition. In some embodiments, the weighting vector may have at least some components that are greater than at least some other components within the weighting vector. In yet another method, the sample vector includes a component identified as a fiducial point for the sample vector, and the weighting vector has a peak component corresponding to the fiducial point within the sampled vector, the peak component having a greater amplitude than other components of the weighting vector.

Another illustrative embodiment includes a method of determining whether a patient is undergoing a malignant cardiac condition comprising capturing a cardiac signal having a cardiac event from a patient using implanted electrodes, sampling the cardiac signal such that it is comprised of a number of signal samples, and comparing the cardiac signal to a stored template to yield a score indicative of correlation between the cardiac signal and the stored template, wherein at least some of the signal samples are provided with greater weight during the comparison and others of the signal samples are provided with a lesser weight during the comparison. In one embodiment, the cardiac signal includes a fiducial point, and greater weight is given to samples nearer the fiducial point than other samples. In another embodiment, the cardiac signal includes one or more slopes, wherein lesser weight is given to samples taken along a sloped portion of the cardiac signal.

Yet another illustrative embodiment includes a method of cardiac signal analysis, the method comprising capturing a cardiac signal by the use of first and second electrodes disposed within a patient, detecting a cardiac event, conditioning a portion of the cardiac signal associated with the cardiac event, and analyzing the portion of the cardiac signal to determine whether the patient is likely experiencing a malignant cardiac condition. The step of detecting a cardiac event may include observing whether a captured cardiac signal exceeds a threshold value in the following manner: after a previous cardiac event, selecting a refractory period; identifying peak signal amplitudes of one or more previous cardiac events and selecting first and second thresholds related to the peak signal amplitudes, the first threshold having a greater value than the second threshold; and generating the threshold value with a continuously decreasing value over a time following the refractory period and before sensing of a next cardiac event, the threshold value having a first value equal to the first threshold and, at a later point in time, having a value approaching the second threshold.

In some embodiments, the first threshold is at least 50 percent of an average of a number of previous peak signal amplitudes. In yet additional embodiments, the second threshold is less than 10 percent of an average of a number of previous peak signal amplitudes. These values may be adaptive, for example, one percentage or the other may vary over time if false detections are identified. The step of analyzing may include comparing the cardiac signal to a stored template and providing greater weight to comparisons of first corresponding portions of the cardiac signal and the template, and lesser weight to comparisons of second corresponding portions of the cardiac signal and the template. The first corresponding portions may correspond to greatest amplitude portions of the cardiac signal. The second corresponding portions may correspond to greatest slope regions of the cardiac signal. The step of analyzing may include observing whether certain portions of the cardiac signal have a magnitude that exceeds a sample threshold and, if not, replacing those portions of the cardiac signal with a preselected value.

BRIEF DESCRIPTION OF THE DRAWINGS

FIG. 8 shows mathematical treatment of a sample using a weighting matrix; and

DETAILED DESCRIPTION

The following detailed description should be read with reference to the drawings. The drawings, which are not necessarily to scale, depict illustrative embodiments and are not intended to limit the scope of the invention.

To date, implantable cardiac treatment systems have been either epicardial systems or transvenous systems. For example, transvenous systems can be implanted generally as shown in FIG. 1B. However, as further explained herein, the present invention is also adapted to function with a subcutaneous implantable cardiac treatment system as shown in FIG. 1A.

Figure 1A:
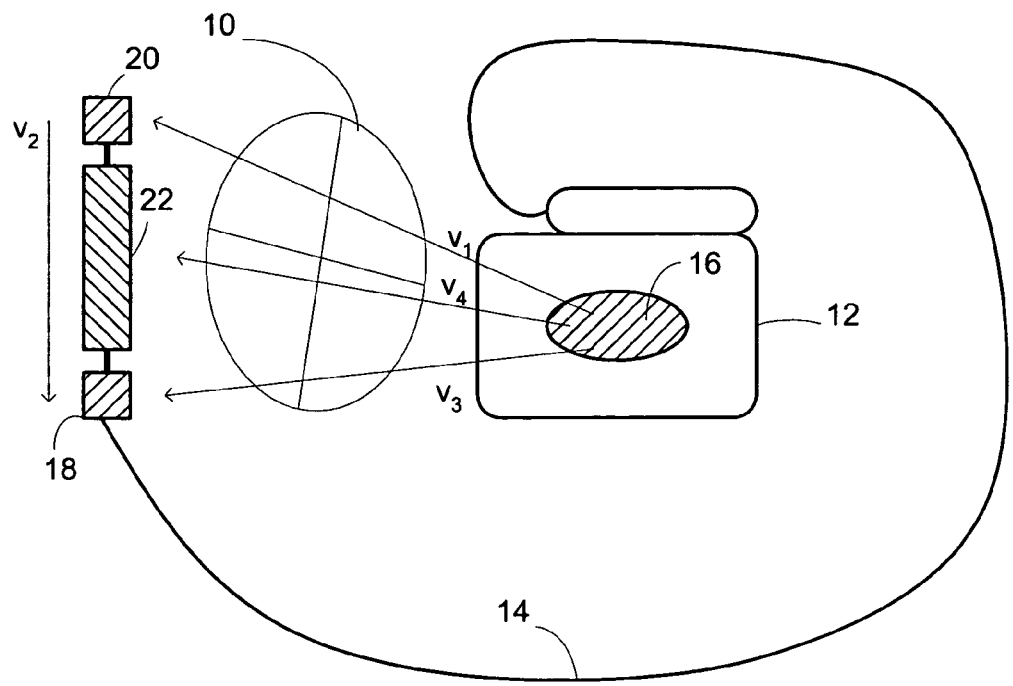
FIGS. 1A and 1B illustrate two example configurations for implantable cardiac treatment devices.
Figure 1B:
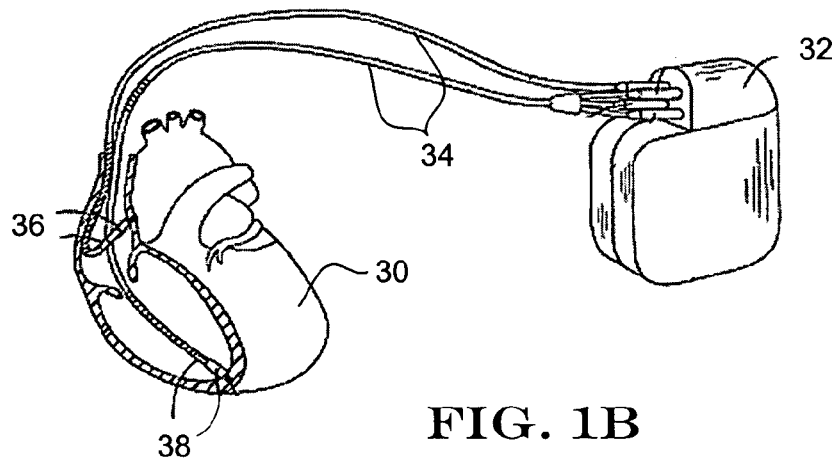

FIG. 1A illustrates a subcutaneously placed implantable cardiac treatment system, in particular, an ICD system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The various electrodes define a number of sensing vectors V1, V2, V3, V4. It can be seen that each vector provides a different vector "view" of the heart's 10 electrical activity. The system may be implanted subcutaneously as illustrated, for example, in U.S. Pat. Nos. 6,647, 292 and 6,721,597, the disclosures of which are both incorporated herein by reference. By subcutaneous placement, it is meant that electrode placement does not require insertion of an electrode into a heart chamber, in or on the heart muscle, or the patient's vasculature.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature.

Figure 2:
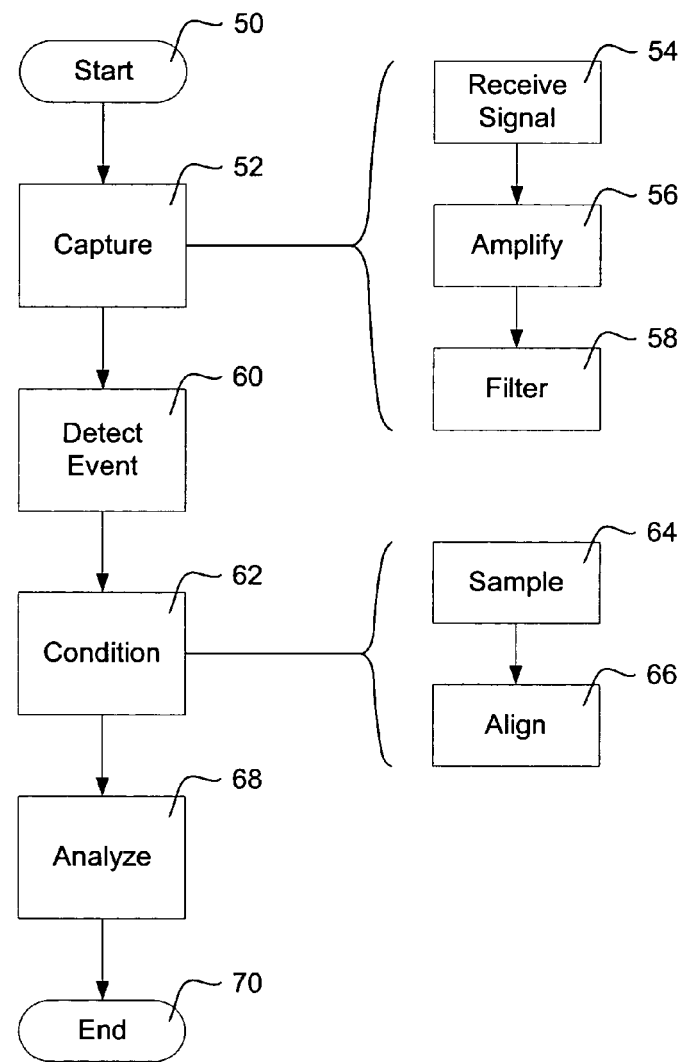
FIG. 2 shows in block form an example of cardiac signal analysis.

FIG. 2 shows in block form an example of cardiac signal analysis. From start block 50, the cardiac signal is captured, as shown at 52. The capture step 52 may include several subparts as shown to the right on FIG. 2. A first step may be receiving a signal 54, which may be performed, for example, using electrodes disposed within a patient as shown in FIGS. 1A-1B, and/or by the use of additional or other suitable implanted electrode configurations. The signal is then amplified to a level more suitable for electrical manipulation, as shown at 56, and filtered to remove known noise (50/60 Hz noise, for example) as well as extraneous data (signals with frequencies above 100 Hz or so, for example), as shown at 58.

After signal capture 52, the next step is to detect whether a cardiac event has occurred, as shown at 60. If so, then the cardiac signal is further conditioned, as shown at 62, which may include sampling 64 to turn the analog signal into a digital signal. Alternatively, event detection may take place using a digitized signal. In some embodiments, the signal is also aligned 66 and placed into a windowed format for further analysis. Some illustrative examples of such alignment are shown in U.S. patent application Ser. No. 10/858,598, filed Jun. 1, 2004 and entitled METHOD AND DEVICES FOR PERFORMING CARDIAC WAVEFORM APPRAISAL, now U.S. Pat. No. 7,248,921, the disclosure of which is incorporated herein by reference.

Once the cardiac event has been conditioned 62, the signal is analyzed, as shown at 68. Analysis may take a number of forms. Rate measurement is one form of analysis; in some prior devices rate measurement was a sole method of analysis. The present invention may include the use of morphology analysis as set forth in U.S. patent application Ser. No. 10/856,084, filed May 27, 2004 and entitled METHOD FOR DISCRIMINATING BETWEEN VENTRICULAR AND SUPRAVENTRICULAR ARRHYTHMIAS, now U.S. Pat. No. 7,330,757, the disclosure of which is incorporated herein by reference.

The present invention, in several embodiments, provides additional details to parts of the method shown in FIG. 2. In one example embodiment, the step of detecting an event 60 may include comparing a received signal to a time-changing event threshold. The method for changing the event threshold may be performed in a manner further set forth below. In another embodiment, the step of conditioning the signal 62 may include an additional step of suppressing certain portions of the signal area of an amplitude that does not exceed a suppression threshold. In another embodiment, the steps of conditioning 62 and/or analyzing 68 may further include weighting the cardiac signal for or during analysis. For example, the cardiac signal may comprise a number of samples, with some samples given greater weight either during conditioning 62 or analysis 68.

Figure 3:
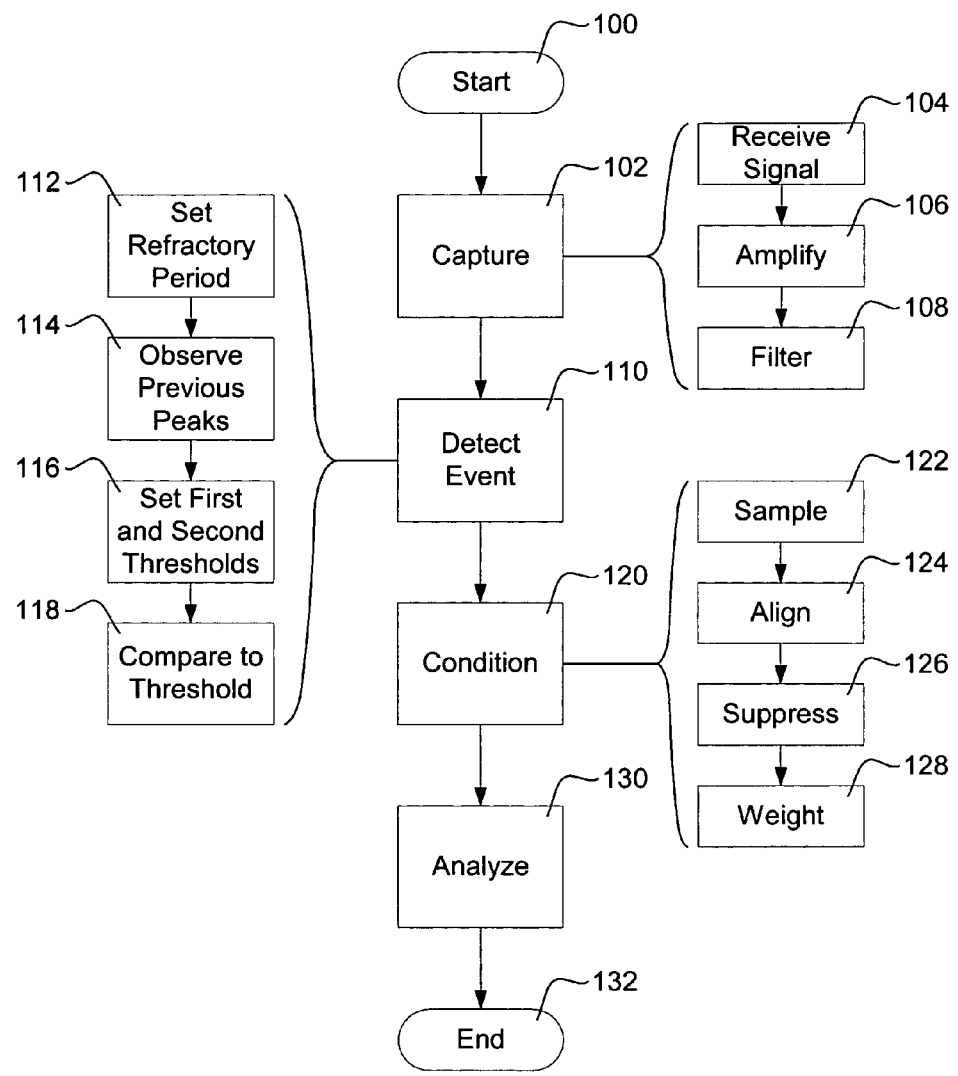
FIG. 3 shows in block form an illustrative embodiment of a method for cardiac signal analysis.

FIG. 3 shows in block form an illustrative embodiment of a method for cardiac signal analysis. The illustrative method of FIG. 3 includes each of the above noted improvements, although it should be understood that the methods, subroutines or sub-methods disclosed herein may be used in combination or separately unless otherwise specified. Further, certain steps may be interchanged or performed in a different order, as desired.

The example method of cardiac signal analysis begins at start block 100 and includes capturing signals, as shown at 102. The capture step 102 may include receiving a signal from implanted electrodes as shown at 104, amplifying the signal as shown at 106, and filtering the signal as shown at 108. The amplify and filter steps 106, 108 may be interchanged, and additional filtering stages may be provided.

Once a signal has been captured at 102, the method continues with detecting an event, as shown at 110. The step of detecting an event may include a subroutine as shown on the left of the Figure. The subroutine may include, after sensing a previous event, setting a refractory period, as shown at 112. During the refractory period, an event will not be detected. Also included in the event detection subroutine is the step of observing previous peak amplitudes, as shown at 114. First and second thresholds are set using the previous peak amplitudes, as shown at 116. In an illustrative example, the first threshold is a threshold level above which detection occurs shortly after the end of the refractory period, and the second threshold is a threshold level above which detection occurs later on in time. A linear or exponential curve may be used to define the threshold. In some embodiments, the first threshold is a first, relatively higher percentage of an average of at least two previous peaks, and the second threshold is a second, relatively lower percentage of an average of at least two previous peaks. A constant may be added to either threshold. Further explanation of an illustrative threshold is provided below by reference to FIG. 4.

With the thresholds set, the event detection subroutine then includes comparing a received signal to the threshold, as shown at 118. When the received signal exceeds the threshold, an event may be declared. If desired, an event or waveform appraisal method may be used in addition to that shown, for example, methods of validation such as those set forth in U.S. patent application Ser. No. 10/858,598, filed Jun. 1, 2004 and entitled METHOD AND DEVICES FOR PERFORMING CARDIAC WAVEFORM APPRAISAL, now U.S. Pat. No. 7,248,921, the disclosure of which is incorporated herein by reference.

After an event has been detected at 110, the method continues by conditioning a received signal corresponding to the detected event, as shown at 120. The conditioning step 120 may include a subroutine as shown to the left in the Figure. The cardiac signal may be sampled, as shown at 122, to digitize the analog signal. Next the sampled signal may be aligned for purposes of comparing the signal to a saved cardiac template, as shown at 124.

Within the conditioning step 120, the sampled cardiac signal may undergo a suppression step as shown at 126. For example, a threshold below which samples are "zeroed" out may be defined. If a correlation analysis comparison with a template is used, then the suppression step may reduce the effects of noise on analysis. Next, the sampled, aligned, and suppressed cardiac signal may be subjected to a weighting step, as shown at 128. During the weighting step 128, certain samples are given greater analytical weight than other samples.

After the conditioning step 120, the method next includes analyzing the signal, as shown at 130. Analysis may include, for example, comparison to a stored or dynamic template. Analysis may also include other morphology or rate considerations, such as measurement of R-R intervals or QRS width. The method of processing and analyzing the cardiac signal then ends, as shown at 132. From the method of FIG. 3, a decision may be made as to whether or not the patient appears to be experiencing a malignant cardiac condition, as well as whether treatment is indicated.

Figure 4:
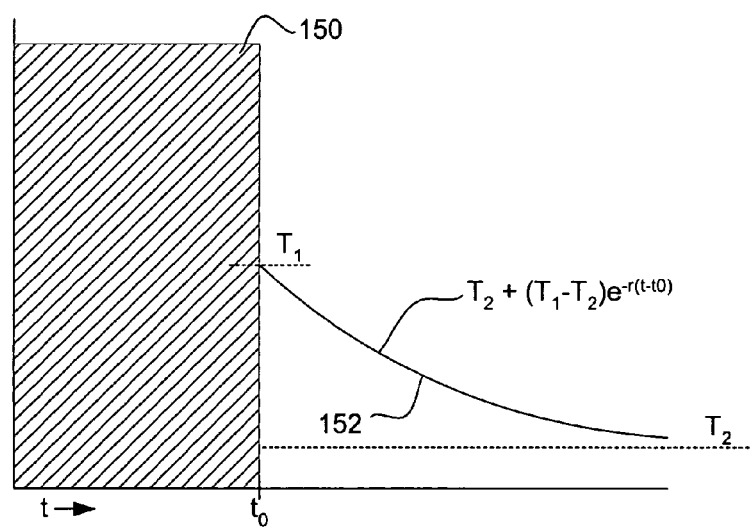
FIG. 4 illustrates, graphically, methods of R-wave detection in accordance with an illustrative method.

FIG. 4 illustrates, graphically, methods of R-wave detection in accordance with an illustrative sub-method. The method is illustrated using a continuous function, although in practice the signal(s) involved often may be discrete, sampled signals. During the illustrative R-wave detection method, a refractory period is represented by block 150, during which the R-wave detector is either disabled or during which detections by the R-wave detector are ignored. After a time $t_0$, a threshold 152 is defined and used. The threshold 152 begins at a first threshold $T_1$ and asymptotically approaches a second threshold $T_2$, following a logarithmic formula as shown in the Figure:

$$\text{Threshold\_152} = T_2 + (T_2 - T_2) * e^{-r(t-t_0)}$$

The first and second thresholds $T_1$ and $T_2$ may be selected as a defined percentage of a previous peak or average of previous peak detected signals.

In one embodiment, the first threshold $T_1$ is set at 35-75% of the average of two previous peaks and the second threshold $T_2$ is set at 2-20% of the average of two previous peaks. In another embodiment, the first threshold $T_1$ is set at 50-60% of the average of two previous peaks and the second threshold $T_2$ is set at 2.5-7.5% of the average of the two previous peaks. In yet another embodiment, the first threshold $T_1$ is set at about 55% of the average of the two previous peaks, while the second threshold $T_2$ is set at about 5% of the average of the two previous peaks. The first and second thresholds may vary, for example, depending upon a patient's heart activity or cardiac signal characteristics, electrode location, or other suitable factors. For example, one or the other of the first and second threshold percentages may be adaptive and may vary depending upon the detected event rate of the patient, the signal-to-noise ratio, or another factor.

By placing the sensing thresholds in the range of a percentage of a recent peak, the R-wave detection method becomes adaptive to changes in patient cardiac electrical activity.

Figure 5A:
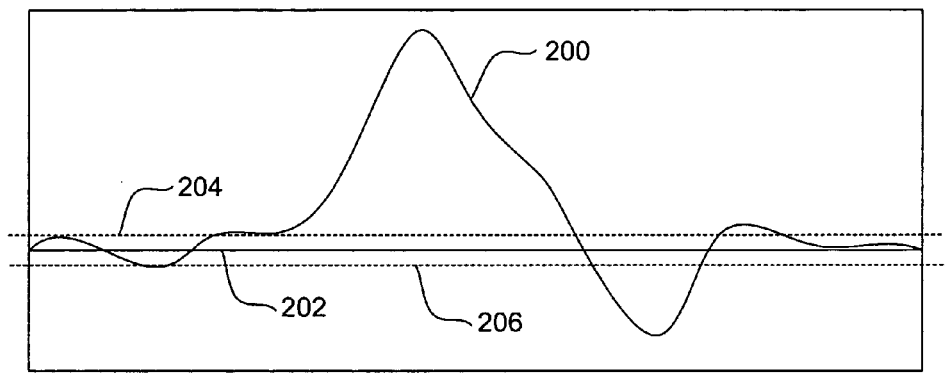
FIGS. 5A-5C show, graphically, an illustrative example method of conditioning a captured cardiac signal.
Figure 5B:
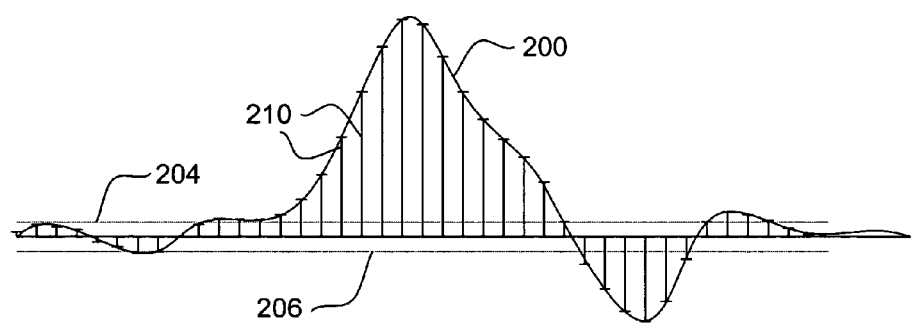
Figure 5C:
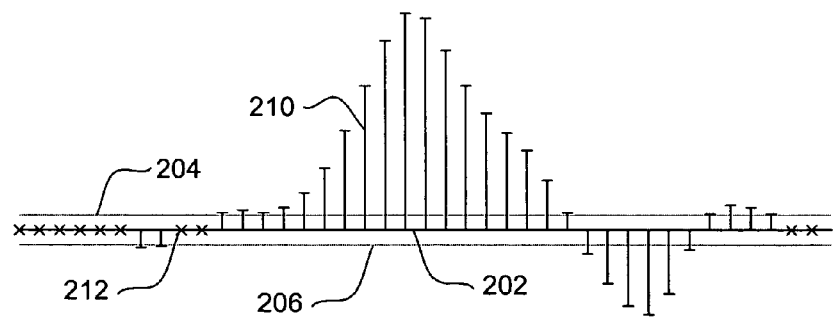

FIGS. 5A-5C show, graphically, an illustrative example method of conditioning a captured cardiac signal. Referring to FIG. 5A, a received signal 200 is shown corresponding to a relatively normal cardiac event having QRS features. The signal 200 is shown in analog form around a baseline 202. Sample thresholds 204, 206 are shown around the baseline 202. FIG. 5B illustrates sampling of the signal 200 of FIG. 5A. It can be seen that samples 210 provide periodic representation of the signal 200, enabling digital manipulation of the signal. Some samples do not exceed the thresholds 204, 206. Referring to FIG. 5C, only the sampled representation 210 is shown. Some of the samples have been replaced by "X" symbols, such as samples 212. These samples are samples which did not exceed the thresholds 204, 206 and have therefore been replaced, using the illustrative method, with the baseline value.

The thresholds 204, 206 are shown as symmetric thresholds about a baseline 202. In other embodiments, the thresholds 204, 206 may be asymmetric instead. In some embodiments, an absolute value may be taken, rather than signed values, as shown, such that only one threshold is defined. The thresholds 204, 206 may be set to a value that is sufficiently low that it may be surmised that, rather than cardiac signal, a sample falling within the thresholds 204, 206 is dominated by noise. In some embodiments the thresholds are set to constant levels. Alternatively, thresholds 204, 206 can be set to a percentage in the range of 1% to 5% of peak signal amplitude or adaptive over time using, for example, knowledge of the received cardiac signal. In the digital domain, another threshold level may be to make use of the digital characteristics of the signals once sampled. For example, in a system having 256-step resolution (an 8-bit system) operating on absolute values, samples with values between 0000 0000 and 0000 1000 may be set to 0000 0000. In another embodiment, signals falling below threshold 204 and above baseline 202 may be set to the value of threshold 204, and signals falling above threshold 206 and below baseline 202 are set to the value of threshold 206.

Figure 6A:
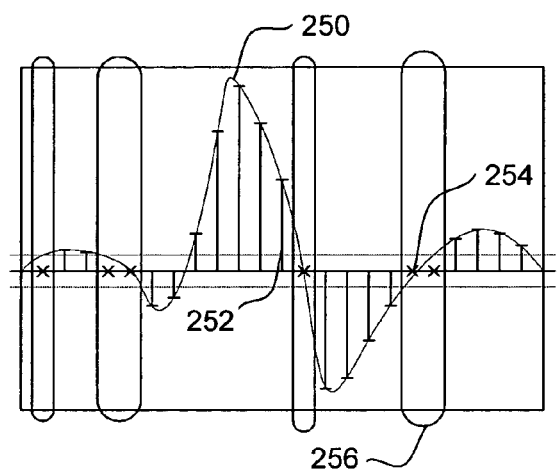
FIGS. 6A-6B illustrate another thresholding operation.
Figure 6B:
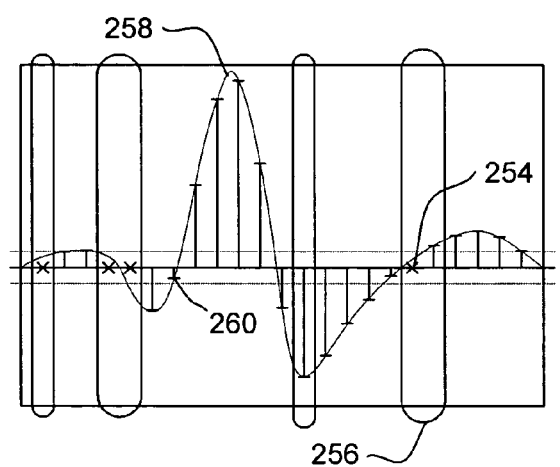

FIGS. 6A-6B illustrate another thresholding operation. FIG. 6A illustrates thresholding performed on a template. The template signal 250 is illustratively shown, with samples 252 representing the actual template. The template may be used for comparing to a received signal for the purpose of determining whether the received signal likely corresponds to a malignant cardiac event. Some samples 254 are shown "zeroed out" to the baseline value in a method according to that discussed by reference to FIGS. 5A-5C. These samples are marked, as indicated by thresholding block 256.

Referring to FIG. 6B, treatment of a received signal 258 is shown. It can be seen that a sample 260 falls between the sample thresholds and the baseline. However, sample 260 does not fall within a thresholding block 256, and so the threshold comparison is not performed for this sample. Instead, for samples within the thresholding block 256, the threshold comparison is performed, and sample 254 is zeroed out. The method of FIGS. 6A-6B thus calls for marking which samples have been subjected to thresholding in the template of FIG. 6A for the purpose of conditioning the received sample 258 in FIG. 6B.

Figure 7:
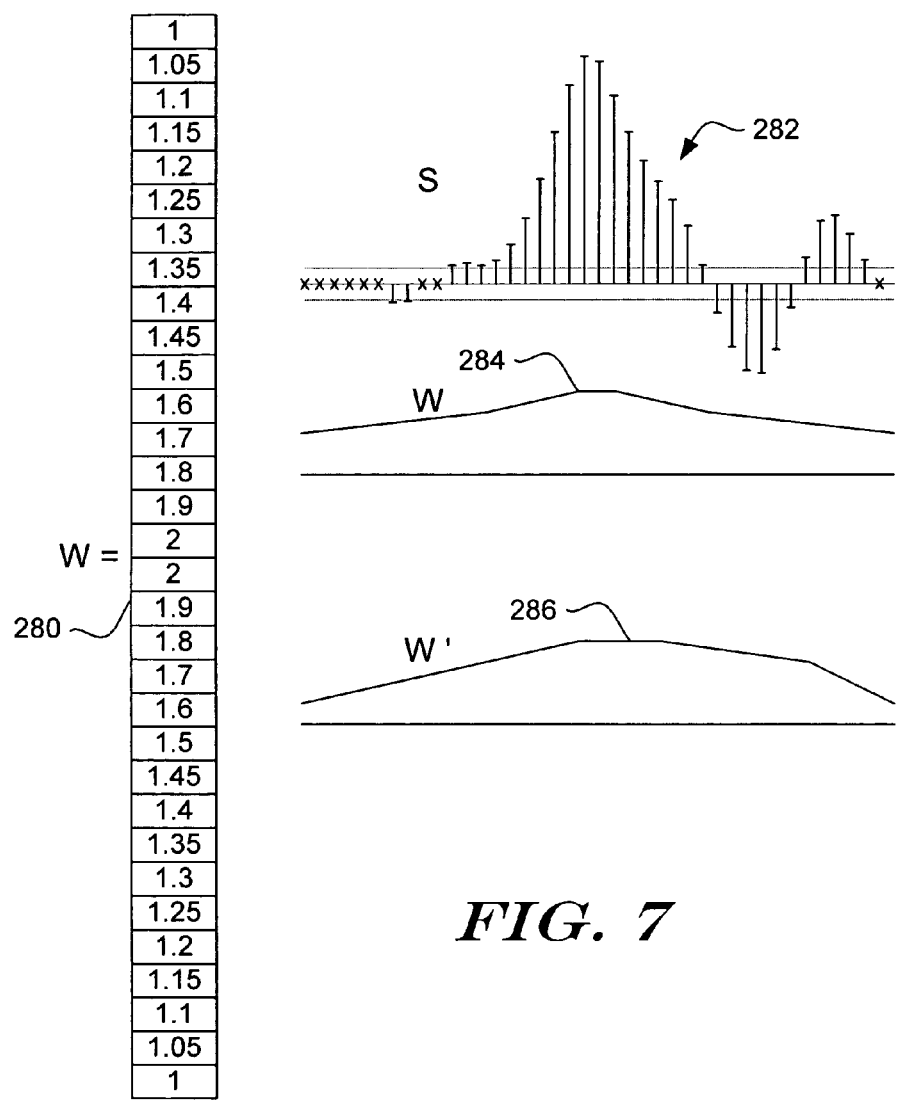
FIG. 7 shows in graphical and numeric format some example embodiments for weighting vectors.

FIG. 7 shows in graphical and numeric format some example embodiments for weighting vectors. A weight vector W 280 is shown numerically as including a number of values. In the illustrative example, signal S includes a number of samples 282, with the size of the weight vector 280 being chosen to correspond to the number of samples 282. The graphical form of W is shown at 284. It can be seen that the greatest weight is given to samples in the center of the signal S. One reason to place greater weight in this region of the signal S is that the center portion of the received signal may likely contain more dramatic morphology data assuming that some semblance of a QRS-type cardiac event can be detected. Further, this region may be emphasized as it is the region where greatest deviation from the baseline, and the signal most likely to contain the least relative amount of noise, can be found.

By the use of a vector cross product, the signal S can be modified using the weight vector 280. With the method of FIG. 7, additional analysis may include correlation waveform analysis. An example formula for such analysis is the following:

$$\text{CWA\_Score}(\%) = 1 - \frac{\sum_i |a * (t_i) - s_i|}{\sum_i |a * (t_i)|} * 100$$

where: $t_i$ is the value of the $i^{th}$ template sample, $s_i$ is the value of the $i^{th}$ signal sample, a is a scaling factor calculated as a ratio of the signal peak to the template peak, and i is the number of samples in the template and signal. The use of a weighting factor as part of signal conditioning is based on application of the formula:

$$s_i = w_i \times r_i$$

where $w_i$ is the value of the $i^{th}$ weighting factor and $r_i$ is the value of the $i^{th}$ unweighted or raw data sample. Likewise for the template:

$$t_i = w_i \times tr_i$$

where $tr_i$ is the raw template value.

FIG. 8 shows mathematical treatment of a sample using a weighting matrix. The mathematical operation of FIG. 8 is greatly simplified for illustrative purposes. In essence, the template vector 290 is crossed with a diagonal weighting matrix 292 having diagonal values corresponding to the weighting vector to yield a weighted template vector 294. Likewise, the cross product of the sample vector 296 with the diagonal weighting matrix 292 yields a weighted sample vector 298. The weighted template vector 294 and weighted sample vector 298 may then be used in further analysis.

While FIGS. 7-8 assume that signal conditioning is used to provide the weighting function, the signal may also be provided with added weight during analysis. Returning to the above formula for CWA, a weighting vector may be taken into account in the formula:

$$\text{CWA\_Score}(\%) = 1 - \frac{\sum_i |w_i * [a * (t_i) - s_i]|}{\sum_i |w_i * a * (t_i)|} * 100$$

Again, $w_i$ is the value of the $i^{th}$ weighting factor. With the above formula, the weighting vector can be used to modify the CWA analysis.

Figure 9:
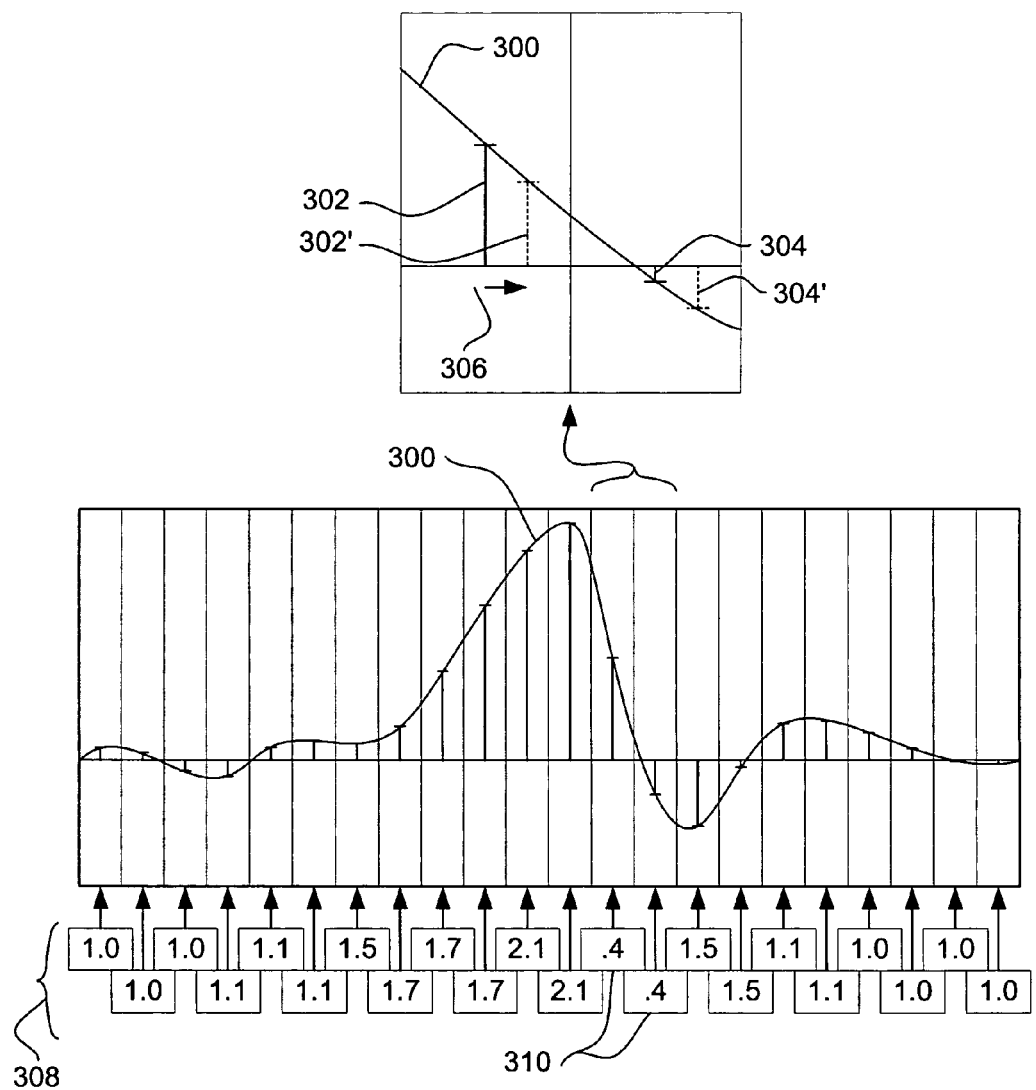
FIG. 9 illustrates another approach to a weighting vector/operation.

FIG. 9 illustrates another approach to a weighting vector/operation. A signal 300 is shown sampled in a number of sample blocks. After a peak, signal 300 drops off with a large downward slope. A portion of the signal 300 is shown blown up in the upper portion of FIG. 9. There it can be seen that samples 302 and 304 are taken of signal 300. However, a slight change of timing, indicated by skew 306, results in samples 302', 304', rather than samples 302, 304. This means that, due to the steep slope of signal 300, a small skew of the sampling results in a significant change of the samples, with sample 302' having a smaller magnitude and lower value, while sample 304' has a greater magnitude and more negative value. The skewing of the samples causes one sample to have a lesser amplitude and lesser magnitude, while the other has a more negative amplitude and greater magnitude. The weighting vector, however, which is shown at 308, may account for the likelihood of such effects along the steepest slope region. Specifically, it can be seen that the least weight is given by the portion 310 of the weighting vector 308 corresponding to the steep slope. Meanwhile, at more gradually sloped locations, higher weight is given. The example shown in FIG. 9 is merely another illustrative manner in which a received signal may be weighted.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of determining whether a patient is undergoing a malignant cardiac condition in an implantable cardiac stimulus device (ICSD) comprising a canister coupled to a plurality of electrodes, the method comprising:
the ICSD capturing a cardiac signal having a cardiac event from a patient using implanted the plurality of electrodes;
the ICSD detecting a cardiac event in the cardiac signal by comparing the cardiac signal to a detection threshold;

the ICSD sampling and windowing the cardiac signal such that it is comprised of a plurality of signal samples representing a time varying amplitude of the captured cardiac signal during a window of time corresponding to the detected cardiac event; and the ICSD comparing the sampled and windowed cardiac signal to a stored template by determining a difference between a sample value for each sample in the sampled and windowed cardiac signal and a corresponding template value for each sample in the stored template to create a series of difference values, multiplying the series of difference values by a weighting vector to create a series of difference products and summing the series of difference products to yield a score indicative of correlation between the cardiac signal and the stored template, wherein at least some of the signal samples are provided with greater weight and others of the signal samples are provided with a lesser weight by the weighting vector.

2. The method of claim 1, wherein the stored template includes a fiducial point, and the weighting vector is configured such that greater weight is given to samples nearer the fiducial point than other samples.

3. The method of claim 1, wherein the stored template includes one or more slopes, wherein the weighting vector is configured such that lesser weight is given to samples taking taken along a sloped portion of the stored template.

4. An implantable cardiac stimulus device (ICSD) comprising a canister housing operational circuitry and a plurality of electrodes electrically coupled to the operational circuitry, the operational circuitry being configured to perform a method of signal analysis to determine whether a patient is undergoing a malignant cardiac condition comprising:

capturing a cardiac signal from the electrodes;

detecting a cardiac event in the cardiac signal by comparing the cardiac signal to a detection threshold;

sampling and windowing the cardiac signal such that it is comprised of a number of signal samples representing a time varying amplitude of the captured cardiac signal during a window of time corresponding to the detected cardiac event; and comparing the sampled and windowed cardiac signal to a stored template by determining a difference between a sample value for each sample in the sampled and windowed cardiac signal and a corresponding template value for each sample in the stored template to create a series of difference values, multiplying the series of difference values by a weighting vector to create a series of difference products and summing the series of difference products to yield a score indicative of correlation between the cardiac signal and the stored template, wherein at least some of the signal samples are provided with greater weight and others of the signal samples are provided with a lesser weight by the weighting vector.

5. The ICSD of claim 4 wherein the operational circuitry is further configured to identify a fiducial point based on the stored template, and the weighting vector gives greater weight to samples nearer the fiducial point than other samples.

6. The ICSD of claim 4 wherein the operational circuitry is further configured such that the weighting vector gives lesser weight to samples taken along a sloped portion of the stored template.

* * * * *

UNITED STATES PATENT AND TRADEMARK OFFICE
CERTIFICATE OF CORRECTION

PATENT NO. : 8,014,851 B2
APPLICATION NO. : 11/527184
DATED : September 6, 2011
INVENTOR(S) : Alan H. Ostroff, James W. Phillips and Venugopal Allavatam It is certified that error appears in the above-identified patent and that said Letters Patent is hereby corrected as shown below:

Column 8, lines 64 to 65, claim 1:

from a patient using implanted the plurality of electrodes;

Is corrected to:

from a patient using the plurality of electrodes;

Column 9, lines 26 to 27, claim 3:

configured such that lesser weight is given to samples taking taken along a sloped portion of the stored template.

Is corrected to:

configured such that lesser weight is given to samples taken along a sloped portion of the stored template.

Signed and Sealed this
Twenty-fifth Day of September, 2012

David J. Kappos
*Director of the United States Patent and Trademark Office*